United States Patent [19]
Akiyama

[11] Patent Number: 4,991,954
[45] Date of Patent: Feb. 12, 1991

[54] OPHTHALMIC DISEASE DETECTION APPARATUS

[75] Inventor: Kouichi Akiyama, Tokyo, Japan

[73] Assignee: Kowa Company Ltd., Japan

[21] Appl. No.: 430,062

[22] Filed: Oct. 30, 1989

Related U.S. Application Data

[63] Continuation of Ser. No. 196,006, May 19, 1988, abandoned.

[30] Foreign Application Priority Data

| May 20, 1987 | [JP] | Japan | 62-121414 |
| May 20, 1987 | [JP] | Japan | 62-121415 |
| May 20, 1987 | [JP] | Japan | 62-121416 |

[51] Int. Cl.⁵ ............................................. A61B 3/10
[52] U.S. Cl. .................................... 351/221; 351/214
[58] Field of Search ............... 351/205, 214, 215, 221; 128/303.1

[56] References Cited

U.S. PATENT DOCUMENTS

| 4,208,107 | 6/1980 | Oharek | 351/215 |
| 4,711,542 | 12/1987 | Ichihashi et al. | 351/221 |
| 4,838,683 | 6/1989 | Ichihashi et al. | 351/221 |

*Primary Examiner*—Paul M. Dzierzynski
*Attorney, Agent, or Firm*—Bruce L. Adams; Van C. Wilks

[57] ABSTRACT

An apparatus for detecting ophthalmic diseases such as an inflammation in a patient's eye which includes means for focusing a linearly polarized laser beam at a selected spot in the eye. The light scattered from the eye is photoelectrically detected and converted into an electrical signal which is subsequently used to determine the protein concentration essential to ophthalmic disease detection in the patient's eye. The laser beam of linear polarization projected on the spot to be measured only contains substantially the same linear polarization component as that contained in the light scattered from the patient's eye. In the apparatus, light adjusting and/or regulating means are provided to adjust the quantity of light impinging on a detector or the intensity of the laser beam produced from the laser source.

3 Claims, 8 Drawing Sheets

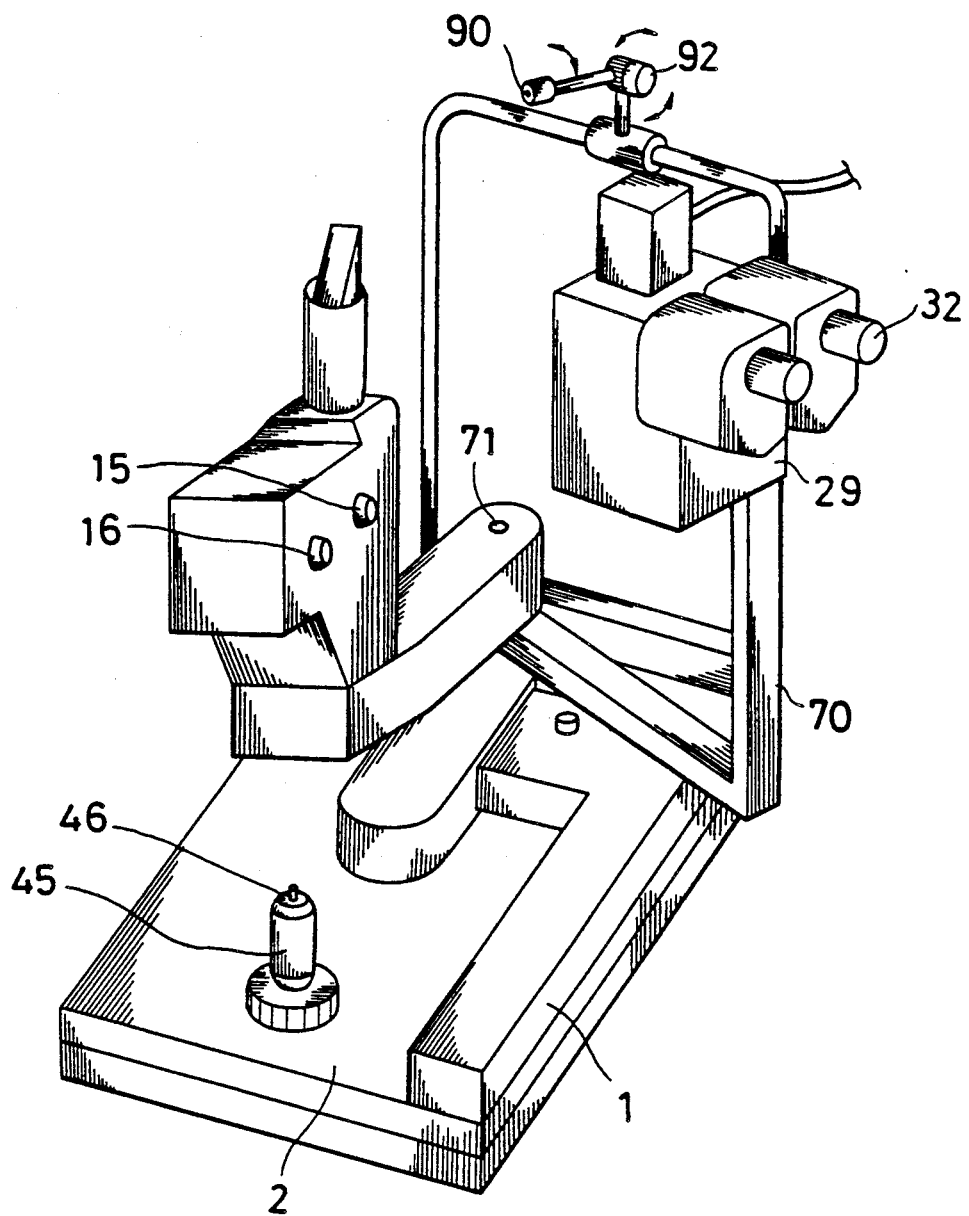
F I G. 1

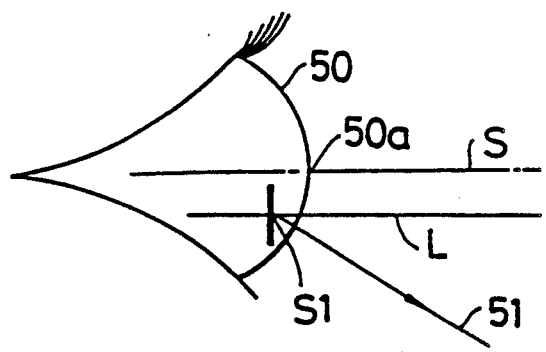
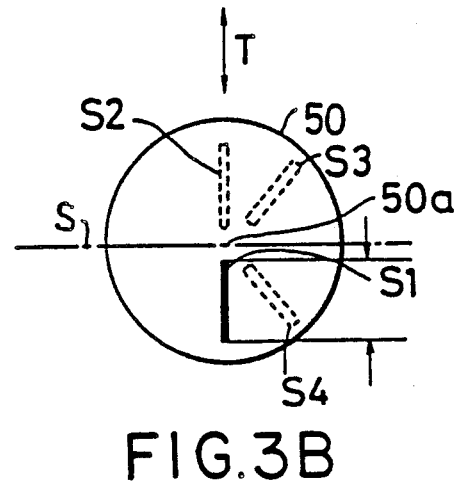
FIG. 3A  FIG. 3B
FIG. 4
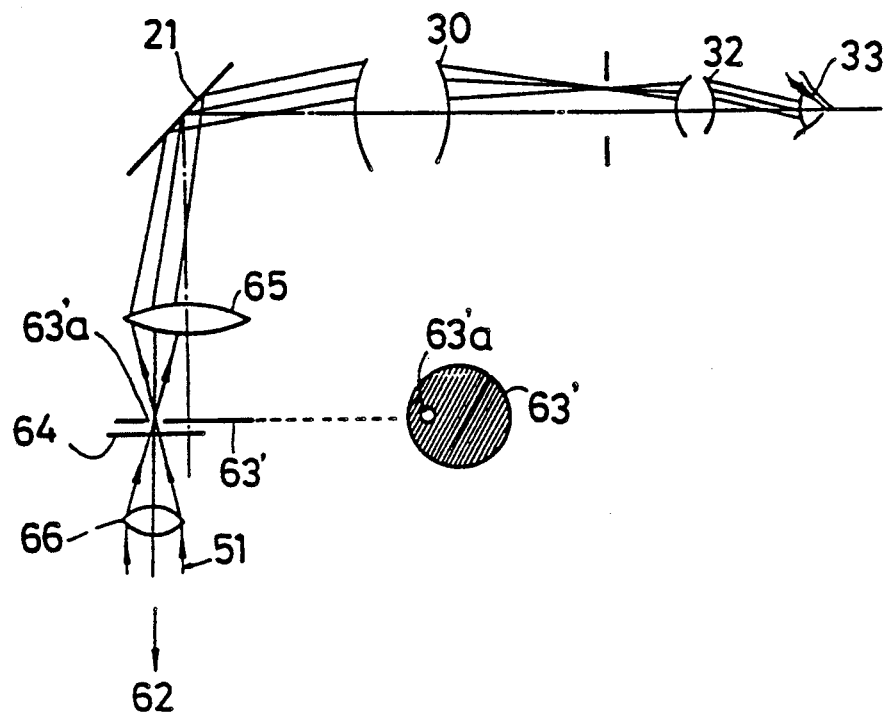

OPHTHALMIC DISEASE DETECTION APPARATUS

This is a Rule 62 continuation of application Ser. No. 196,006 filed May 19, 1988 now abandoned which claims priority of Japanese Patent Applications Nos. 121414/87, 121415/87 and 121416/87, all filed May 20, 1987.

BACKGROUND OF THE INVENTION

1. Field of the Invention

This invention relates to an apparatus for detecting ophthalmic diseases in a patient's eye, and more particularly to an apparatus for detecting ophthalmic diseases in which laser light is radiated via an optical system at one spot in the camera oculi of the patient's eye, particularly in the anterior chamber thereof and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of ciliary body, iris, and the front surface of the crystalline lens, while the camera oculi posterior is defined by a space surrounded by the rear surface of the iris, inner surface of the ciliary body, and front surface of the crystalline lens. The camera oculi is filled with transparent humor aqueous, which has chemical and physical characteristics different from lymphatic liquid and has a close relation with the metabolism of the cornea or crystalline lens. The humor aqueous contains proteins which increase causing the camera oculi to be turbid when it becomes inflamed.

In this respect, the measurement of protein concentration in the camera oculi of the patient's eye is of great importance in determining whether the camera oculi is inflamed, that is, whether a blood-aqueous barrier functions normally or not.

To measure the protein concentration in the camera oculi, a slit lamp microscope is very often used to determine the turbidity by grading via naked eyes. This is, however, disadvantageous because the judgment depends upon the person who performs the measurement.

On the other hand, a photographic measuring method has been developed to make a quantitative measurement of the protein concentration. This method is, however, too complicated to analyze, thus very difficult to apply in a clinical examination.

To overcome this problem, an apparatus for detecting the ophthalmic diseases has been proposed which includes means for focusing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

This apparatus, however, has also the drawback that the light reflected or scattered at the cornea, iris, lens or artificial lens after an operation to remove cataracts impinges on the spot to be measured in the anterior chamber or intrudes into the laser scattered light in the form of noise. This disadvantageously makes the measurement inaccurate and the measured value poorly repeatable. This problem is further exacerbated by a varying intensity of the laser beam produced from the laser source due to fluctuating energy power or because a photodetector for receiving the scattered light changes in its sensitivity.

The apparatus has further such a drawback that the high intensity of laser light burdens the patients during a measurement.

SUMMARY OF THE INVENTION

It is therefore an object of the present invention to provide an apparatus for detecting ophthalmic diseases which is capable of easily and precisely measuring the protein concentration in a patient's eye.

It is another object of the present invention to provide an apparatus for detecting ophthalmic diseases which is capable of reducing a burden on the patient.

It is still another object of the present invention to provide an apparatus for detecting ophthalmic diseases which is capable of adjusting the intensity of laser beam produced from a laser source.

It is still another object of the present invention to provide an apparatus for detecting ophthalmic diseases which is capable of compensating for the irregularities of sensitivity of a photodetector for receiving the light scattered from the patient's eye.

In accordance with the present invention, the ophthalmic disease detection apparatus disclosed herein includes a laser source for producing a linearly polarized laser beam, a laser beam projector for projecting the laser beam, means for focusing the laser beam at a selected spot in the patient's eye, means for receiving light scattered from the spot in the patient's eye and photoelectrically converting it into an electrical signal, and means for processing the electrical signal to evaluate the ophthalmic diseases in the patient's eye. The laser beam projector and light receiving means are arranged so that their optical axes cross substantially at right angles with each other. The laser beam projected on the spot only contains substantially the same linear polarization component as that contained in the light scattered from the patient's eye.

The laser beam projector and the light receiving means are usually so arranged that their axes cross about at 90 degrees. In this case, the light receiving means receives the laterally scattered light that contains only an S-polarized component. In the above-mentioned arrangement, the laser beam projected into the patient's eye contains only the same polarization component(S) as that of the scattered light, so that the P-polarized component can be removed from the laser beam, thus allowing the quantity of laser light to be reduced by that factor. This arrangement, thus, permits the employment of a compact laser source of low power, low costs and the reduction of a burden on the patient.

The laser beam is, preferably, so deflected that it scans an area in the patient's eye except for a plane which is perpendicular to the scanning direction and includes the corneal vertex of the patient's eye.

The laser beam projector includes a polarizing beam splitter which is disposed so that said laser beam of linear polarization impinges thereon in the form of P-polarization.

The polarizing beam splitter is used to combine the optical axes of the laser beam projector and an illumination light projector into one optical axis.

The apparatus for detecting ophthalmic diseases in a patient's eye according to the present invention further includes means for adjusting the quantity of light impinging on the light receiving means so that the light receiving means produces a predetermined output when it receives a predetermined intensity of scattered light.

This arrangement makes it possible to compensate the irregularities of sensitivity of the light receiving means and to assure the precise measurement of the disease in the patient's eye.

The adjusting means is realized by a neutral density filter or linear polarizing plate.

The apparatus according to the present invention further includes means for regulating the quantity of laser light produced from the laser source so as to be substantially constant independently of a fluctuation in power of the laser source. In this arrangement, it is possible to produce the laser beam whose intensity is almost constant even if the energy power of the laser beam fluctuates, thus also assuring an improved, precise ophthalmic disease detection of good reproducibility.

The regulating means can be realized by a neutral density filter of variable transmittivity, or a polarizing plate.

BRIEF DESCRIPTION OF THE DRAWINGS

The objects and features of the present invention will become more apparent from a consideration of the following detailed description taken in conjunction with the accompanying drawings in which:

FIG. 1 is a perspective view of the detection apparatus according to the present invention;

FIGS. 3(A) and 3(B) are schematic explanatory views relating to laser beam scanning width;

FIG. 4 is a view showing the arrangement of an optical system for observation of corneal reflex light;

DETAILED DESCRIPTION OF THE PREFERRED EMBODIMENTS

Figure 2:
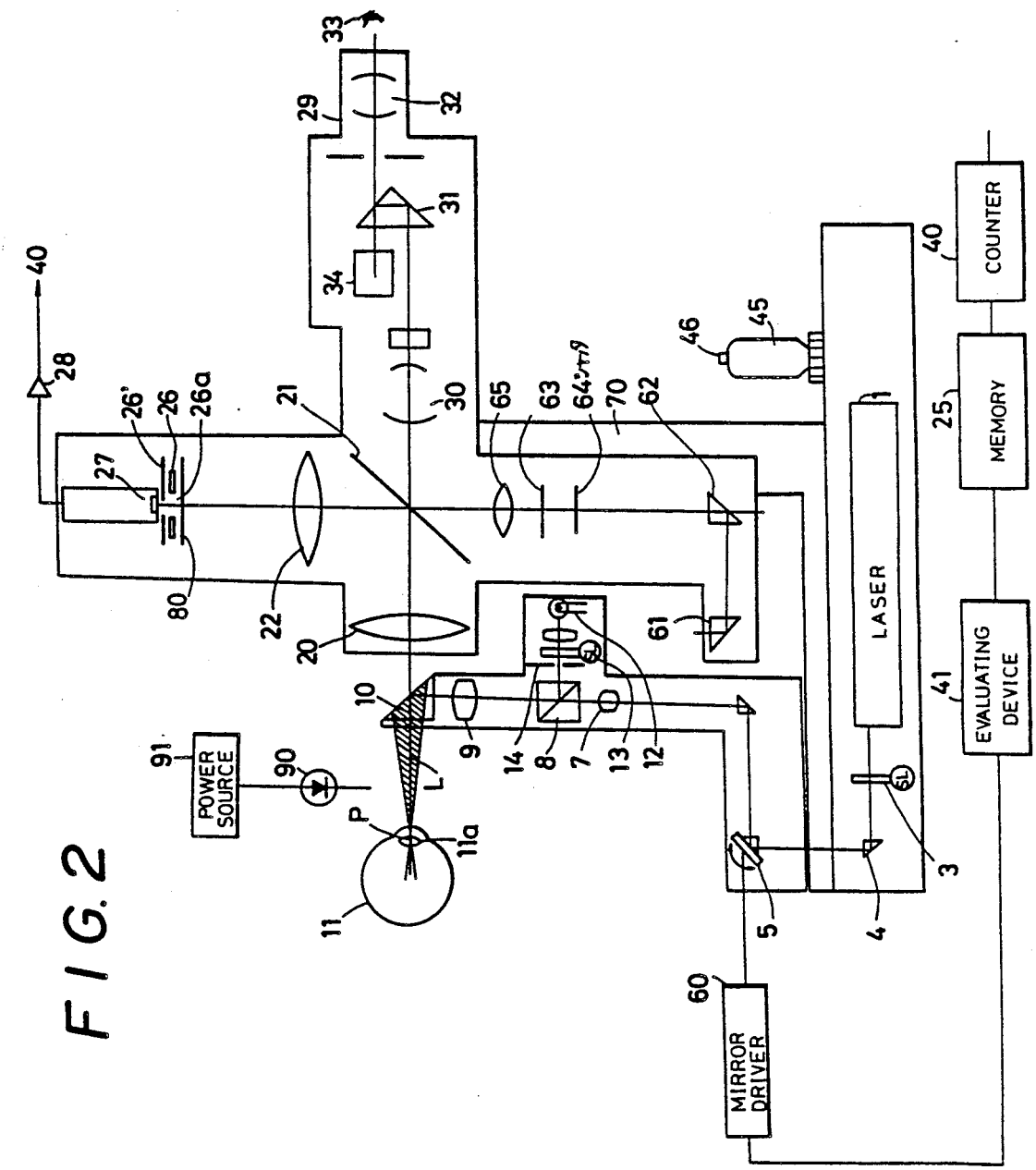
FIG. 2 is a block diagram showing the arrangement of the optical systems of the apparatus.

FIGS. 1 and 2 show the general arrangement of an ophthalmic disease detection apparatus according to the present invention. In the drawings, reference numeral 1 indicates a helium-neon or argon type laser light source which can produce a linearly polarized laser beam. The laser light source 1 is provided on a base 2. The laser beam of linear polarization emitted from the laser light source 1 is passed through a laser filter 3, a prism 4, a swingable mirror 5, a prism 6, a lens 7, a beam splitter 8, a lens 9 and a prism 10, and converged at one spot in a camera oculi 11a of patient's eye 11.

A slit light source 12 is provided in laser emitting portion, and the light emitted from this slit light source 12 passes through a slits light shutter 13, a slit 14, and via the beam splitter 8, the lens 9 and the prism 10, whereupon it is imaged as a slit image on the camera oculi 11a or anterior chamber. Because the light emitted from the above mentioned laser light source 1 is converged as a spot of light, the slit light image is intended to illuminate the periphery of the light spot and thereby make the verification of the location of the spot image easy.

Adjustment as well as switching of the length of the slit along the lengthwise dimension of the slit 14 are carried out by means of an adjusting knob 15 and a switching knob 16, respectively.

Part of the laser light scattered from the spot being measured in the camera oculi 11a passes through the objective lens 20 of a detector 29, and is then divided by a beam splitter 21, whereupon a portion of the light passes through a lens 22, light quantity adjuster 80 such as an ND filter, linear polarizer and the like, and a shutter 26', and strikes a photomultiplier 27 which performs the function of a photoelectric converter. A mask 26 with slits 26a having a certain width is disposed in the front of the photomultiplier 27, to limit the impinging of the scattered light thereon. Another portion of the scattered light divided by the beam splitter 21 is directed in another direction and passes through a variator lens 30, a prism 31, and a monitoring plate 34. The image may be observed by an examiner 33 through an eyepiece 32.

The output signal of the photomultiplier 27 is amplified by an amplifier 28 and then applied to a counter 40 for counting the number of photons, thus determining the intensity of the scattered light detected by the photomultiplier 27. The counter 40 counts the number of pulses appearing. When the photomultiplier 27 receives the scattered light greater in intensity than a predetermined value, the counter 40 counts the output signal from the photomultiplier 27, so that the intensity of the scattered light is detected as the number of pulses per unit time. The output signal of the counter 40, indicating the sampled number or total number of pulses is stored in an area of a memory 25 for each unit time. The signals stored in the memory 25 are read out and then applied to an evaluating device 41 to calculate the protein concentration in the camera oculi 11a.

The swingable mirror 5 is pivoted by a mirror driver 60 connected to an evaluating device 41 whereupon the laser beam is thereby diverted so as to move or scan the spot of laser light within the anterior chamber. As shown in FIGS. 3(A) and 3(B), the scanning of the laser beam takes place over a region S1 which is below a plane S which is perpendicular to the scanning direction T and includes the vertex 50a of the cornea 50. The plane S is selected so as not to coincide with a plane L (shown in FIG. 2 and FIG. 3(A)) that includes the optical axes of the laser beam projector and the light receiving means. The detector 29 houses an optical system for the positional alignment of the patient's eye 11 with the detection apparatus by receiving the corneal reflected light 51. The corneal reflected light 51 is received via a prism 61, passes through a prism 62, a shutter 64, a mask 63 and a lens 65, and is deflected by the beam splitter 21 toward the examiner 33. The prisms 61 and 62 are adjusted so as to receive the corneal reflected light with good efficiency. The shutter 64 is linked to the shutter 26' disposed in front of the photomultiplier 27, the arrangement being such that when the shutter 26' is open the shutter 64 is closed.

The detector 29 is affixed to a support 70. The support 70 and the laser beam projector are provided so as to be rotatable, with respect to each other, about a spindle 71, so as to allow the angle between the optical axes of the laser beam projector and the light receiving means to be adjusted to the required setting. In the preferred embodiment, detection is carried out with this angle set at about 90 degrees.

In accordance with this invention, an eye fixation light 90 consisting of a light-emitting diode or the like powered by electricity supplied from a power source 91 is disposed at a position that permits fixation of the patient's eye. The light selected for the eye fixation light 90 is of a different color than the light of the laser light source 1. For example, when the light from the laser light source is red, a green light is selected. The eye fixation light 90 can be turned in the direction indicated by the arrow (FIG. 1) by means of a link mechanism 92 to enable it to be adjusted so that it is always in an optimum position with respect to the patient's eye.

Provided on the base 2 is an input means, such as a joystick 45 equipped with a push-button 46, and this can be operated to insert the laser filter 3, the slit light shutter 13, the shutter 26' and the shutter 64 into, or retract the elements from, the respective optical system.

The operation of the detection apparatus arranged thus will now be described. In conducting the detection, the slit light source 12 is activated and an image of the slit 14 is formed, via the beam splitter 8, the lens 9 and the prism 10, on a part that includes the measuring point P (FIG. 2) of the anterior chamber 11a. Following this, light from the laser light source 1 is converged on the measuring point P via the said optical system.

A portion of the light from the measuring point P is simultaneously directed by the beam splitter 21 to the examiner 33 for observation and through the lens 22, the light quantity adjuster 80, the mask 26 and the shutter 26' to impinge on the photomultiplier 27.

Figure 7:
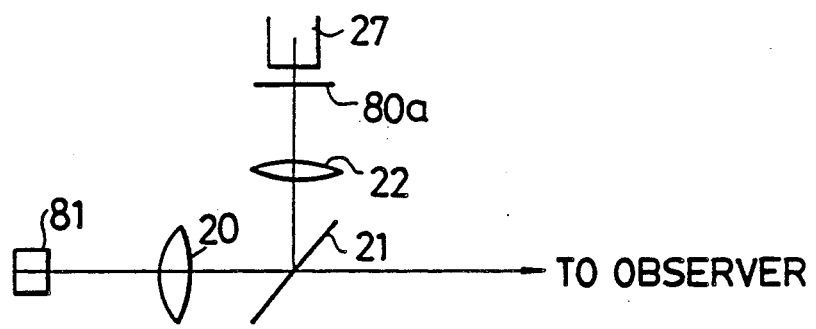
FIGS. 7 to 9 are schematic explanatory views each showing a different embodiment of an optical system for adjusting the quantity of light impinging on a photodetector.

As shown in FIG. 7, the light quantity adjuster 80 is, for example, comprised of a neutral density filter 80a and disposed in the front of the photomultiplier 27 to compensate for irregularity in its sensitivity. For this purpose, a sample cell 81 is used which contains a liquid such as polystyrene latex having a given intensity of scattered light to provide a reference concentration. A laser beam having a certain intensity is projected into the sample cell and scattered towards the photomultiplier 27. The transmission factor of the neutral density filter 80a is so selected that the output signal from the photomultiplier 27 may be equal to a set value. The neutral density filter 80a whose transmission factor is thus determined makes it possible to compensate for the irregularity of the photomultiplier in its sensitivity.

The swingable mirror 5 (FIG. 2) is pivoted by the mirror driver 60 in the direction indicated by the arrow, to scan the laser beam in the direction T across a scanning width S1 which is below the plane S which includes the corneal vertex, as illustrated in FIG. 3(B).

The photomultiplier 27, whose sensitivity is compensated by the light quantity adjuster, receives, via the slit 26a, the incident scattered laser light, detects the intensity of the light that has been diffused by protein particles in the anterior chamber 11a and converts this into a corresponding pulse train which is counted by a counter 40 as a number of pulses per unit time and the count values are stored in memory 25 allocated for each unit time. The evaluating device 41 calculates the data contained in the memory 25 to evaluate the concentration of protein in the anterior chamber.

This embodiment of the invention incorporates a system (elements 61 to 65) for making an exact optical alignment between the portion of the patient's eye to be measured and the light receiving means. With this system, the surface that receives the corneal reflected light 51 is fixed to the laser beam projector or the light receiving means. In the embodiment illustrated in FIG. 2, the prism 61 forms the light receiving surface. During the positional alignment process, the shutter 64 is opened and the shutter 26' is closed. Each of the optical systems is disposed so that when, in this state, the patient's eye 11 is correctly aligned with the detection apparatus, the examiner 33 can observe the corneal reflected light within his field of vision.

In this case, as illustrated in FIG. 4, it is preferable to use an arrangement wherein a condenser lens 66 is disposed in front of the shutter 64 and, using the stop 63' that has a transmitting portion or a diffusing surface 63'a, the corneal reflected light 51 is converged on the transmitting portion 63'a. An advantage of this embodiment is that the observed corneal reflected light image is brighter, and as the brightness is related to operating distance, the operating distance can be monitored approximately.

With reference to FIG. 2, the prisms 61 and 62 may be coupled by a light guide and, furthermore, a diffusing plate may be employed in place of the prism 62. Again, because the laser beam projector and the light receiving means are in a predetermined positional relationship (the optical axes thereof set at 90 degrees, for example, as described later), the surface that receives the corneal reflected light may be fixed to the laser beam projector.

Figure 5A:
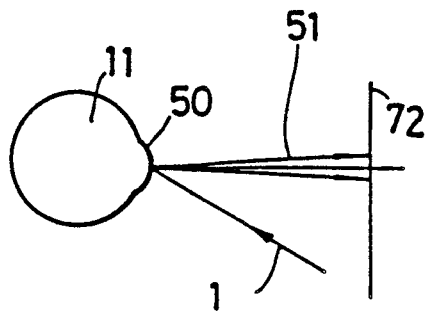
FIG. 5(A) schematic is a view of another embodiment of an optical system for observation of corneal reflex light.
Figure 5B:
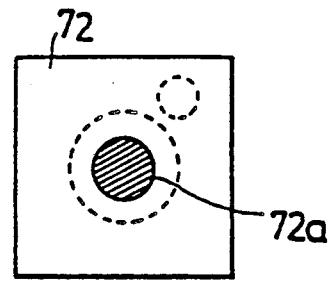
FIGS. 5(B) to 5(D) are schematic explanatory views showing light-receiving plate embodiments.
Figure 5C:
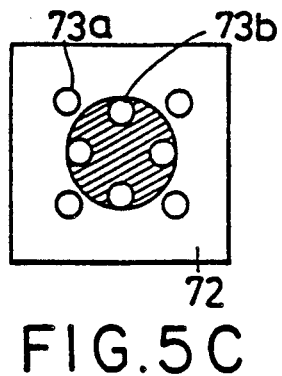
Figure 5D:
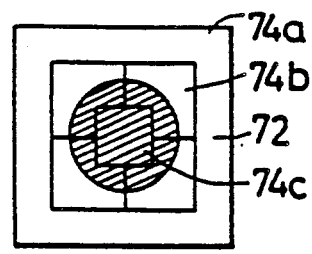

With respect to the positional alignment, as illustrated in FIGS. 5(A) and 5(B), a light receiving plate 72 constituted of ground glass or the like and having a scale with graduations may be used that will enable the examiner to make a direct visual observation. As indicated by the dashed line, the size and position of a corneal reflected light image 72a as observed by the light receiving plate 72 depends on the positional relationship of the patient's eye 11 and the detection apparatus, which makes it possible to carry out the positional alignment by a simple method. Also, as shown in FIGS. 5(C) and 5(D), it is possible to dispose a plurality of photodiodes on the light receiving plate 72 for positional alignment purposes. In the example illustrated by FIG. 5(C) the detection apparatus is in alignment when no light is received by the four photodiodes 73a and light is received by the four photodiodes 73b. In the example shown in FIG. 5(D) alignment has been achieved when light is not received by photodiode 74a and light is received by the four-part photodiode 74b and photodiode 74c.

Each of the embodiments illustrated in FIG. 5 enables three-dimensional positional alignment to be carried out using a simple arrangement and eliminates the need for registration light sources, targets and other such parts relating to laser beam projector systems for positional alignment. Also, when photodiodes are employed, it is possible to have the photodiodes indicate the positional alignment in accordance with the received light state.

With the radius of curvature of the cornea being around 6 mm to 8 mm, and the depth of the aqueous humor in the anterior chamber being in the order of 3 mm, the rays that are brought to convergence on the aqueous humor of the anterior chamber are, after reflection at the cornea, once converged and then diffused. Utilizing this converged light spot for positional alignment is convenient for obtaining positional alignment information because the spot has a high luminance, but as in the case of some detection areas in the aqueous humor the light might be converged quite close to the cornea, for the light receiving surface it is preferable to choose a place where the light has become diffused.

Figure 6:
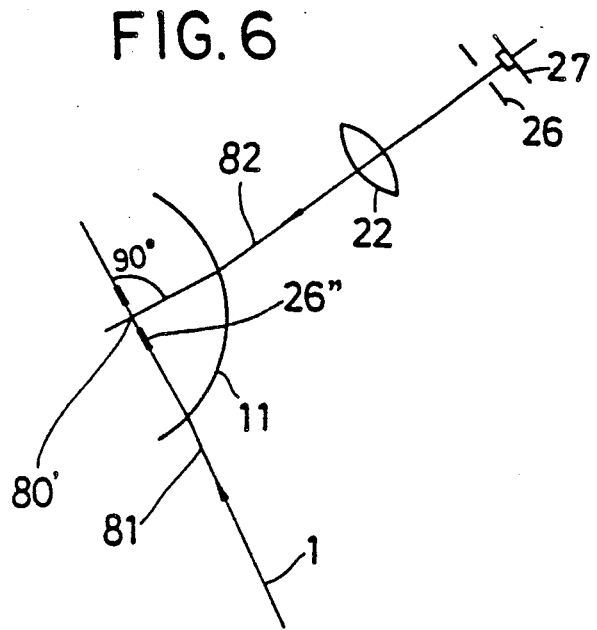
FIG. 6 is a schematic view showing the positional arrangement when the optical axes of the laser beam projector and the light receiving means are disposed at about 90 degrees to each other.

Also in accordance with this embodiment, as illustrated in FIG. 6 the light receiving means and the laser beam projector are disposed so that their optical axes cross at around 90 degrees. At this time an image 26″ is formed at the beam waist 80 on the optical axis of the light receiving means at a position which is a conjugate with that of the mask 26.

Figure 8:
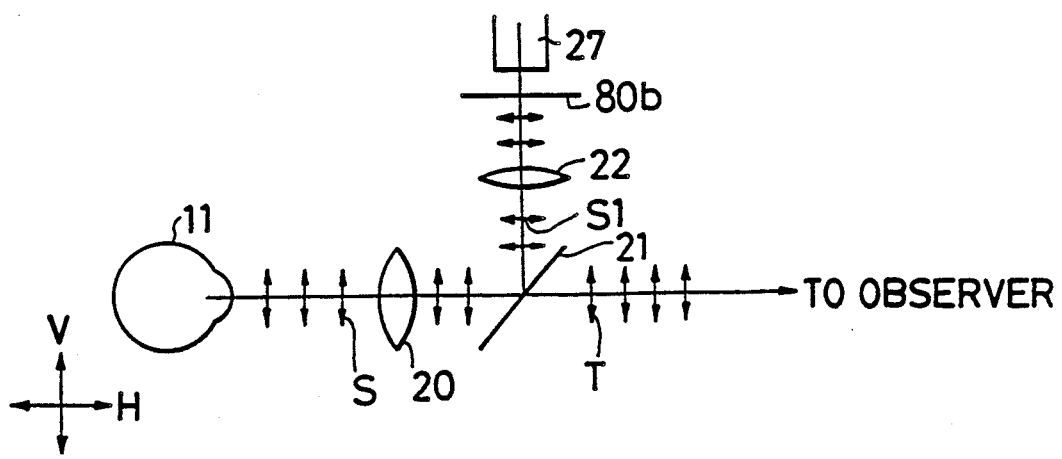

FIG. 8 shows an embodiment in which the light quantity adjuster consists of a linear polarizer (plate) 80b. The light scattered at the proteins in the camera oculi of the patient's eye 11 is almost S-polarized, so far as it concerns the lateral scattering. For this reason, the polarizer 80b is rotated to adjust the quantity of light impinging on the photomultiplier 27. Similarly as in FIG. 7, the reference cell 81 is used to determine the angle of rotation of the polarizer 80b so that the output of the photomultiplier 27 may be equal to a set value.

Figure 9:
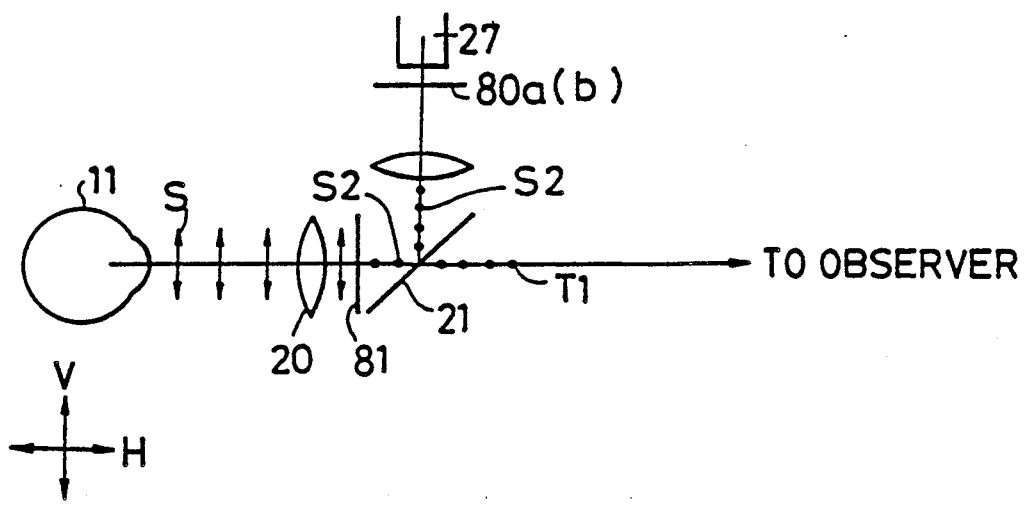

The scattered light from the proteins in the camera oculi behaves P-polarized when it impinges on the semitransparent mirror 21. This leads to the greater quantity of transmitted light T and the smaller quantity of reflected light S1. To prevent this, a half-wavelength plate 81 is disposed in the front of the semitransparent mirror 21 as shown in FIG. 9 to cause the scattered light to impinge on the semitransparent mirror as S-polarized light. The scattered light, when it passes through the half-wavelength plate, has its direction of polarization perpendicular to the plane of paper with an improved S/N ratio because of the great reflected light S2 and the small transmitted light T1.

Figure 10:
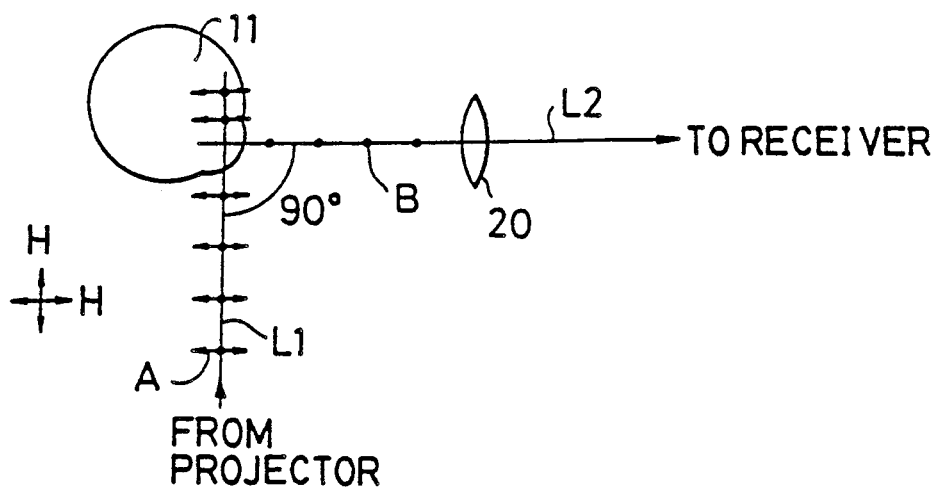
FIG. 10 is a schematic explanatory view showing the projection and reception of a laser beam having P and S components.

In the above described embodiment, the laser beam projector L1 and the light receiving means are so arranged that their axes cross about at 90 degrees as shown in FIG. 10. In this case, the light receiving means receives the laterally scattered light that contains substantially only the S-polarized component (linear component perpendicular to the plane of paper). Thus, the use of a laser source which emits a random polarized laser beam causes its P-polarized component A (indicated by double arrow) to pass through the patient's eye with the result of a burden to the patient and a reduced efficiency of the laser source in use.

To remove this drawback, the laser beam of linear polarization produced by the laser light source is so produced that the laser beam impinging on the patient's eye 11 may contain substantially only the S-polarized component corresponding to the linear polarization of the scattered light. In other words, the direction of polarization of the linearly polarized laser beam is substantially the same direction on the spot to be converged as that of linear polarization of the scattered light.

Since, in this arrangement, the laser beam from the laser light source 1 contains only the S-polarized component, it is possible to reduce the incident light quantity by a factor corresponding to the P-polarized component thereof.

In the above-mentioned embodiment, a halogen lamp is used as slit light source 12, so that the reduction of quantity of laser light can be prevented if the polarizing beam splitter is used to combine both the optical axes of the laser beam and slit light into one optical axis. It will be noted that the laser beam impinges on the polarization beam splitter 8 in the form of P-polarization. This makes it possible to prevent the loss of the linearly polarized laser beam when it passes through the beam splitter.

Thus, the laser beam contains only the polarization component (S) that the lateral scattered light has, and the P-polarized component has been removed from the laser beam, thus allowing the quantity of laser light to be reduced by that factor. This permits the use of the compact laser light source of low power, low costs and the reduction of a burden to the patient's eye.

In the embodiments as described above, the laser light source suffers from a power fluctuation of several percentages. This also causes fluctuation in intensity of light scattered from the patient's eye. This fluctuation leads to errors in measurement, reduced reproducibility and degraded accuracy of measurement because of a strong correlation between the intensity of scattered light and the concentration in the camera oculi.

Figure 11:
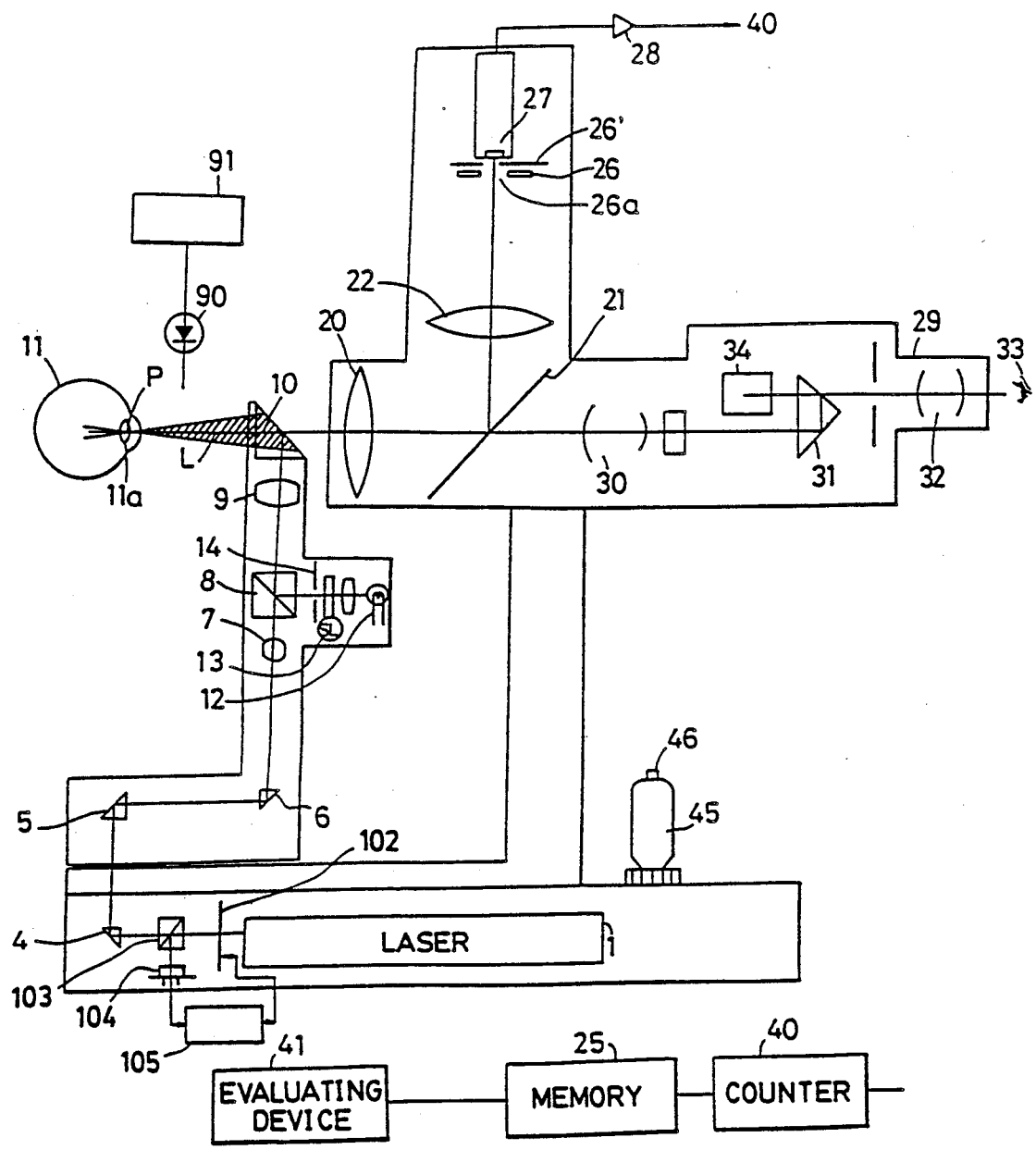
FIG. 11 is a block diagram showing another embodiment of the optical system according to the present invention.

This problem can be solved by an embodiment in FIG. 11 in which a light quantity adjuster is provided in the laser beam projector to adjust the quantity of laser light projected onto a predetermined portion in the eye so as to be substantially constant independently of the power fluctuation of the laser light source. In the embodiments in FIG. 11, the same portions as those in FIG. 2 are indicated by the same reference numerals, and their description will be omitted.

In FIG. 11, the laser beam from the laser light source is converged on a spot in the camera oculi 11a of the patient's eye via a light quantity adjuster 102 such as a polarizing plate, a neutral density filter of variable transmittivity and the like, a beam splitter 103, the prisms 4 to 5, the lens 7, the beam splitter 8, the lens 9 and the prism 10. A portion of laser light split by the beam splitter 103 is directed toward for example, a photodiode 104 which serves to monitor the quantity of light from the laser light source. The output from the photodiode 104 is fed to an automatic light regulator 105 whose output is fed back to the light quantity adjuster 102 for automatic regulation of light quantity.

Figure 12A:
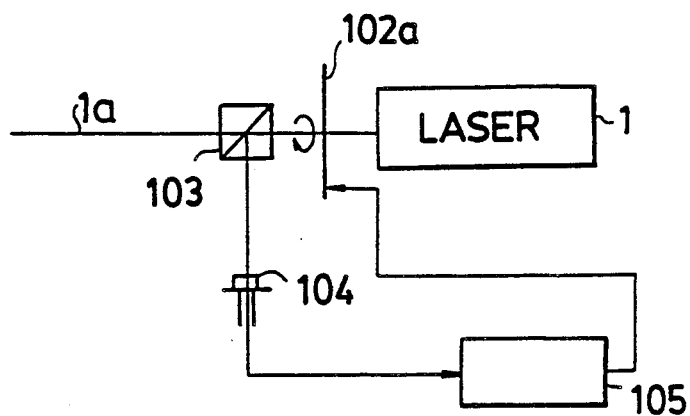
FIG. 12(A) is a schematic explanatory view showing an arrangement in which a polarizing plate is used as a light quantity adjuster.
Figure 12B:
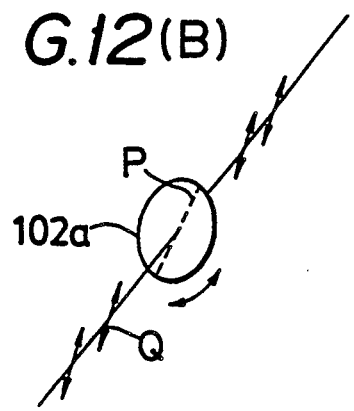
FIG. 12(B) is a schematic explanatory view showing the regulation of light using polarization characteristics of a polarizing plate.

The light quantity adjuster 102 is, for example, constructed of a polarizing plate 102a, which will be mounted about the optical path 1a of the laser light source 1 as shown in FIG. 12 (A). The polarizing plate 102a has the direction P of polarization as shown in FIG. 12 (B), while the laser light source 1 of He-Ne has the linear polarization Q. Thus, the rotation of the polarizing plate 102a makes it possible to adjust the quantity of light passing therethrough.

The output signal from the photodiode 104 is applied to the light regulator 105 including a motor, which is then actuated to rotate the polarizing plate 102a so that the quantity of light impinging on the photodiode 104 may be constant. The polarizing plate 102a is, for example, rotated in the direction in which its polarization P coincides with the direction Q of polarization of the laser beam, if an increase of the light quantity is desired, and rotated in the direction in which both the directions P and Q cross at 90 degrees, if a decrease is desired.

Thus, the laser beam converged on the spot P to be measured can be made constant in quantity of light irrespectively of the power fluctuation of the laser light source.

Figure 13A:
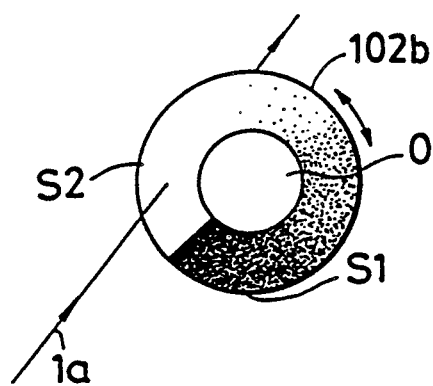
FIGS. 13(A) and 13(B) are schematic explanatory views each showing a light regulation using a neutral density filter.
Figure 13B:
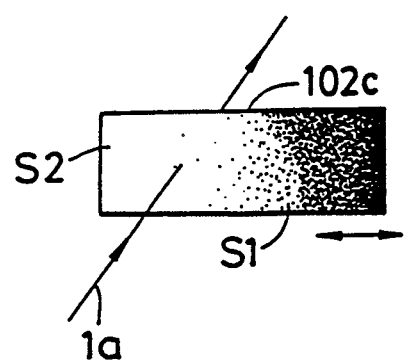

FIG. 13(A) and 13(B) show each of embodiments in which the light quantity adjuster is comprised of a neutral density filter of variable transmittivity. In this case, the laser light source 1 can have any polarizing characteristics, not limited to the linear polarization. In FIG. 13(A), a neutral density filter 102b is rotated about an axis 0 set off from the optical axis 1a of the laser beam to change its transmission density from S1 to S2. In FIG. 13(B), a neutral density filter 102c is moved into or removed from the optical axis 1a of the laser beam to allow the change in its density.

These neutral density filters 102b and 102c are adapted to be rotatable or slidable so that the quantity of light impinging on the photodiode 104 can be made equal to a set value for automatic light regulation.

In the above embodiments, it will be judged that the laser light source has its time when no set value is obtained even in its maximum power.

These embodiments in which the light quantity adjuster is provided in the laser beam projector assure the compensation for power fluctuation in the laser light source and an improved, precise ophthalmic measurement of good repeatability.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

I claim:

1. An apparatus for detecting ophthalmic diseases in a patient's eye comprising:
   a laser source for producing a linearly polarized laser beam;
   a laser beam projector for projecting said laser beam;
   means for focusing said laser beam at a selected spot in said patient's eye;
   means for receiving light scattered from said spot in the patient's eye and photoelectrically converting it into an electric signal;
   means for processing said electrical signal to evaluate the ophthalmic diseases in the patient's eye;
   means for producing a signal representative of the quantity of laser light produced from said laser source; and
   means responsive to said signal for adjusting the quantity of light produced from said laser source whereby said laser beam is substantially constant independently of a fluctuation in power of said laser source.

2. An apparatus as set forth in claim 1, wherein said adjusting means comprises one of a neutral density filter of variable transmittivity and a polarizing plate.

3. An apparatus as set forth in claim 1, wherein said signal producing means comprises a light monitor downstream of said adjusting means.

* * * * *